(12) United States Patent
Frigg

(10) Patent No.: US 7,887,569 B2
(45) Date of Patent: Feb. 15, 2011

(54) OSTEOSYNTHETIC IMPLANT WITH AN EMBEDDED HINGE JOINT

(75) Inventor: Robert Frigg, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 1970 days.

(21) Appl. No.: 10/735,854

(22) Filed: Dec. 16, 2003

(65) Prior Publication Data

US 2004/0220570 A1   Nov. 4, 2004

Related U.S. Application Data

(63) Continuation of application No. 09/714,147, filed on Nov. 17, 2000, now Pat. No. 6,663,632, which is a continuation of application No. PCT/CH98/00208, filed on May 19, 1998.

(51) Int. Cl.
*A61B 17/80* (2006.01)
(52) U.S. Cl. .................. 606/280; 606/70; 606/283; 606/286
(58) Field of Classification Search .................. 606/61, 606/69–73, 280–299; 623/2.2–2.26
See application file for complete search history.

(56) References Cited

U.S. PATENT DOCUMENTS

| | | | | | |
|---|---|---|---|---|---|
| 1,087,797 | A | * | 2/1914 | Lowe | 273/281 |
| 2,580,821 | A | * | 1/1952 | Toufick | 606/69 |
| 2,628,838 | A | * | 2/1953 | Smalley | 273/271 |
| 2,877,792 | A | * | 3/1959 | Tybus | 137/512.1 |
| 3,599,977 | A | * | 8/1971 | Glass et al. | 273/388 |
| 4,029,091 | A | | 6/1977 | von Bezold et al. | |
| RE31,040 | E | * | 9/1982 | Possis | 623/2.21 |
| 4,361,141 | A | * | 11/1982 | Tanner | 606/61 |
| 4,771,767 | A | * | 9/1988 | Steffee | 606/61 |
| 4,890,845 | A | * | 1/1990 | Gatewood | 273/271 |
| 4,905,679 | A | * | 3/1990 | Morgan | 606/70 |
| 5,053,036 | A | | 10/1991 | Perren et al. | |
| 5,057,111 | A | | 10/1991 | Park | |
| 5,092,320 | A | * | 3/1992 | Maurer | 602/26 |
| 5,380,327 | A | * | 1/1995 | Eggers et al. | 606/69 |
| 5,415,661 | A | * | 5/1995 | Holmes | 606/69 |
| 5,468,242 | A | * | 11/1995 | Reisberg | 606/69 |
| 5,683,465 | A | | 11/1997 | Shinn et al. | |
| 5,731,275 | A | | 3/1998 | Prevost et al. | |
| 5,797,912 | A | | 8/1998 | Runciman et al. | |

(Continued)

FOREIGN PATENT DOCUMENTS

DE   1 949 923   4/1971

(Continued)

*Primary Examiner*—Thomas C Barrett
*Assistant Examiner*—Michael T Schaper
(74) *Attorney, Agent, or Firm*—Fay Kaplun & Marcin, LLP

(57) ABSTRACT

An osteosynthesis implant includes at least one coupling in the form of a swivel joint. Each swivel joint includes at least one planar or annular swivel element and two connecting arms that define a pivot axis. The coupling permits rotation about each pivot axis. The implant and coupling may be formed of unitary construction, or a separate coupling may be connectable to the implant. The coupling may receive a bone fastener such as a bone screw, or may be used in applications that require the coupling to directly support portions of the body such as spinal features.

25 Claims, 5 Drawing Sheets

U.S. PATENT DOCUMENTS

| | | |
|---|---|---|
| 5,807,396 A | 9/1998 | Raveh |
| 5,827,285 A * | 10/1998 | Bramlet ........................ 606/60 |
| 5,916,200 A * | 6/1999 | Eppley et al. ................ 604/178 |
| 6,280,445 B1 | 8/2001 | Morrison et al. |
| 6,315,779 B1 | 11/2001 | Morrison et al. |
| 6,613,728 B1 | 9/2003 | Sirianni et al. |
| 6,627,590 B1 | 9/2003 | Sherry et al. |
| D501,231 S * | 1/2005 | Rom ......................... D21/478 |
| 2002/0058939 A1 | 5/2002 | Wagner et al. |

FOREIGN PATENT DOCUMENTS

| | | |
|---|---|---|
| DE | 24 38 669 | 2/1976 |
| DE | 195 48 395 A1 | 9/1997 |
| WO | WO 88/03781 | 6/1988 |

* cited by examiner

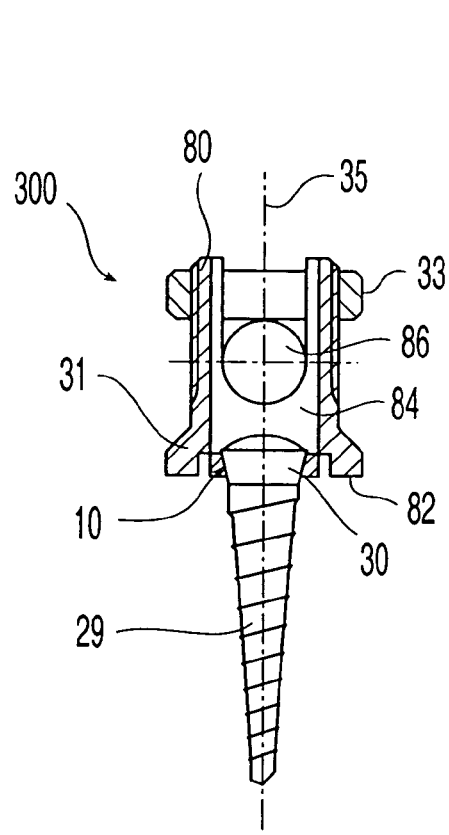
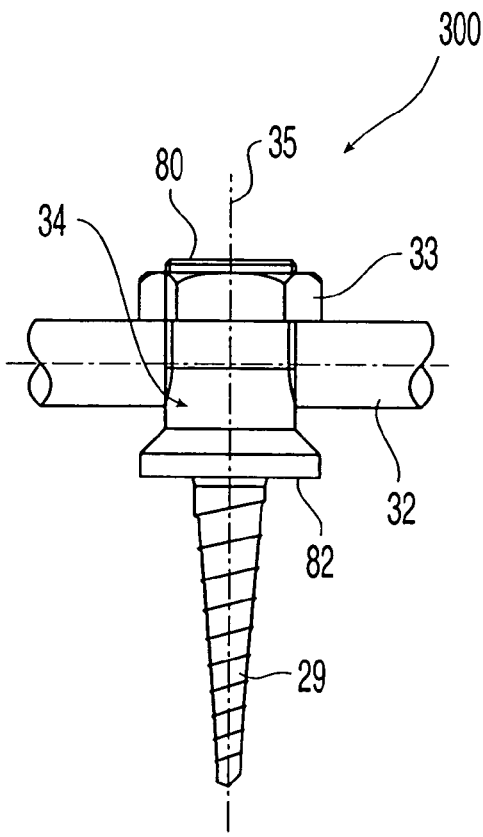
Fig. 4A    Fig. 4B
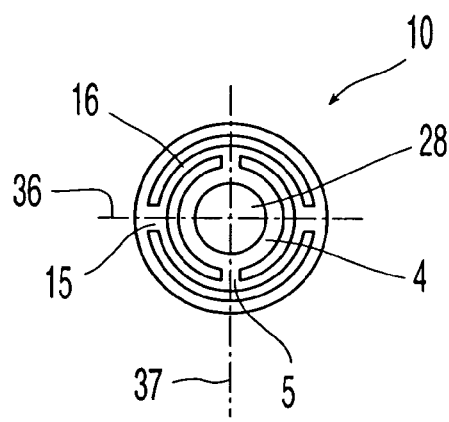
Fig. 4C

OSTEOSYNTHETIC IMPLANT WITH AN EMBEDDED HINGE JOINT

CROSS-REFERENCE TO RELATED APPLICATIONS

This application is a continuation of prior patent application Ser. No. 09/714,147, filed Nov. 17, 2000 now U.S. Pat. No. 6,663,632, which in turn is a continuation of the U.S. National Stage designation of co-pending International Patent Application PCT/CH98/00208, filed May 19, 1998, the entire contents of which are expressly incorporated herein by reference thereto.

FIELD OF THE INVENTION

The invention relates to an implant with a coupling. More particularly, the invention relates to osteosynthesis implants with couplings having gimbal-type swivel joints.

BACKGROUND OF THE INVENTION

Angularly fixed longitudinal supports such as plates and bars increasingly are used in osteosynthesis applications. Such devices are particularly useful for treating fractures that are located near joints, or for anchoring screws in the spinal column. In applications that use short screws, the screws typically can be inserted in the longitudinal support at a preset angle without presenting problems. When longer screws are necessary, a fixed, system-dependent orientation of the screw may be impractical or unwieldy.

To facilitate the use of longer screws in regions such as the spine, special ball joints have been developed. In addition, as disclosed in German patent DE 195 48 395, bone plates have been proposed with specially configured screw holes drilled therein for accepting correspondingly shaped screw heads. The bone screw thus may be locked in place in the bone plate in a relatively randomly selectable orientation. But, the complexity, bulky nature, and insufficient strength provided by the connections of these ball joints and screw head-borehole configurations does not sufficiently remedy the inherent problems encountered with fixed, system-dependent orientations of screws.

Also disclosed in German patent DE 24 38 669 to Bezold is an osteosynthesis bone plate with screw holes having a respective spacing that can be manipulated using externally generated forces. The screw holes are arranged in the form of lugs punched out of the main body of the osteosynthesis plate and connected thereto merely by elastic legs. In one embodiment, the legs are aligned along one axis and connected to the lug diametrically relative to the axis. When the lug is lifted out of the plane of the plate, the legs are bent such that the rotational axis of the lug no longer coincides with the vertical axis of either the lug itself or the screw hole. Use in clinical applications thus is limited because as the lug is turned, the center of the screw hole is undesirably shifted.

There exists a need for a bone plate with a coupling that facilitates the use of a wide range of sizes of bone screws. There further exists a need for a coupling that requires less space than ball joints and provides simplicity in design and use. Additionally, there is a need for a substantially flat swivel joint for use in connecting implant components such as a bone screw and a bone plate.

The present invention provides an implant and coupling capable of furnishing these improvements, and advantageously has application in a wide range of other implants unrelated to bone screw support.

SUMMARY OF THE INVENTION

The present invention relates to an osteosynthesis implant that includes a coupling comprising at least one annular element having a pair of connecting members for coupling the annular element to a surrounding structure. The connecting members provide the annular element with a swiveling motion with respect to the surrounding structure for alignment of the annular element during insertion or implantation of the implant. The connecting members also form a single coupling axis with the surrounding structure and the annular element swivels about that coupling axis.

In one embodiment, the annular element defines a hole for receiving a fastener and the surrounding structure is the implant. Typically, the annular element has a generally circular configuration and defines a generally cylindrical hole that extends along a central axis. Also, the hole is generally perpendicular to at least one of the top and bottom surfaces of the annular element.

In another embodiment, the annular element has a top surface, a bottom surface, and a first thickness defined between the top and bottom surfaces, and the implant has a top implant surface, a bottom implant surface, and a second thickness defined between the top and bottom implant surfaces and the connecting members have a connection thickness. Typically, the first thickness of the annular element is less than or equal to the second thickness of the implant and the connection thickness of the connecting members is also less than or equal to the second thickness of the implant.

In another embodiment, the coupling has inner and outer annular elements where each element has a pair of connecting members and the connecting members of the inner annular element are coupled to the outer annular element and the connecting members of the outer annular element are coupled to a surrounding structure. This permits the inner annular element to be provided with a first swiveling motion and the outer annular element to be provided with a second swiveling motion. Also, the connecting members of the inner annular element form a first coupling axis and the connecting members of the outer annular element form a second coupling axis that is positioned at an angle with respect to the first coupling axis. The first and second coupling axes can be substantially perpendicular to each other.

In another embodiment of the present invention, the inner and outer annular elements, the connecting members and the implant are all formed of unitary construction and each connecting member is capable of exhibiting elastic deformation to permit the annular element to swivel.

In another embodiment, the implant is an intervertebral element having at least one surface that includes the surrounding structure in which the inner and outer annular elements are disposed so that more precise alignment can be provided. In an exemplary embodiment, the intervertebral element has two parallel surfaces, each of which provides the surrounding structure in which the inner and outer annular elements are disposed. The two parallel surfaces define a central longitudinal axis and the intervertebral element has a first through-hole extending generally perpendicular to the central longitudinal axis and has a second through-hole extending generally perpendicular to the first through-hole.

In another exemplary embodiment, the intervertebral element has top and bottom surfaces, each of which provide the surrounding structure in which inner and outer annular elements are disposed. In addition, the top and bottom surfaces are, typically, configured as generally oval plates and are spaced apart from each other with a central connector that is generally cylindrical. Furthermore, the central connector is fixed to the inner annular elements, such that swivelling of the plates is permitted while the inner annular elements remain parallel to each other and the connecting members of the inner annular element form a first coupling axis and the connecting members of the outer annular element form a second coupling axis that is generally perpendicular to the first coupling axis. Typically, the implant is configured and dimensioned to be received between two vertebral bodies.

In another embodiment of the present invention, the surrounding structure in which inner and outer annular elements are disposed is a fixation system for a longitudinal support. The fixation system comprises a mounting head having a top surface and bottom surface, a first head bore which extends from the top head surface to the bottom head surface about a head bore longitudinal axis and a second head bore which extends substantially perpendicular to the first head bore. The second head bore is configured and dimensioned to receive a longitudinal support and the inner annular element includes a hole for a pedicle screw.

BRIEF DESCRIPTION OF THE DRAWINGS

Preferred features of the present invention are disclosed in the accompanying drawings, wherein similar reference characters denote similar elements throughout the several views, and wherein:

FIG. 4A shows a partial cross-sectional view of an additional implant of the present invention in which a swivel joint is integrated in a vertebral fixation element;

FIG. 4B shows a side view of the implant of FIG. 4A;

FIG. 4C shows a top view of a swivel joint used in the implant of FIG. 4A;

DETAILED DESCRIPTION OF PREFERRED EMBODIMENTS

Figure 1A:
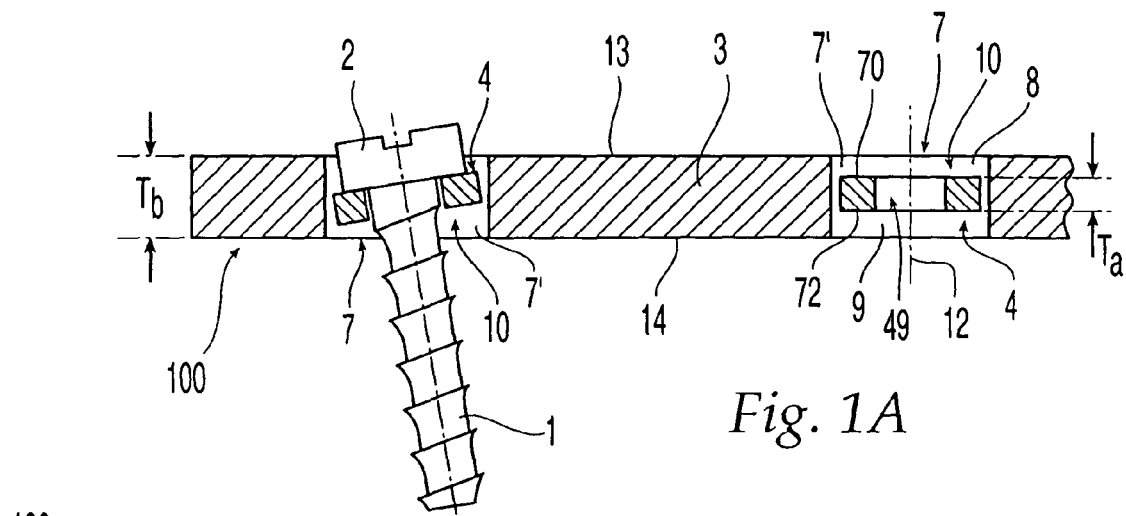
FIG. 1A shows a cross-sectional view of an implant of the present invention in which a swivel joint is integrated in a bone plate.

The present invention relates to an osteosynthetic implant or implant component having at least one swivel joint connected thereto and preferably being in the form of a planar gimbal articulation. The at least one swivel joint preferably includes a planar, disc-shaped or annular swivel element having two flat, bar-shaped connecting elements positioned along a common axis at the outer perimeter of the swivel element. The connecting elements or legs define axes of rotation. Each swivel joint includes at least one swivel element that is rotatably connected to the implant or implant component via the connecting elements. The inner swivel element may be provided with a borehole generally perpendicular to the plane of rotation defined by the axes of rotation of the swivel element. The implant or implant component and the swivel joints may be an integral unit, or connecting legs in the form of pivot shafts may be positioned between the planar or annular swivel joint and the implant in such a fashion that the swivel joint is concentrically supported in a borehole of an osteosynthesis implant component and is rotatable around the pivot axes.

The connecting elements may be dimensioned so that elastic deformation thereof permits an angularly fixed rotation of the swivel element relative to the implant or implant component. The connecting legs are situated opposite each other along one axis, with their outer lateral surfaces attached to the implant or implant component while their inner faces are attached to a planar or annular swivel joint.

In one preferred embodiment, the swivel joint includes two nested, coplanar swivel elements, with each inner swivel element being connected via two connecting elements to a corresponding outer swivel element to permit rotation around a first axis. Likewise, the outer swivel element is connected via two connecting elements to the implant or implant component to permit rotation around a second axis. The axis of rotation may extend between the nested swivel elements along the plane in which the swivel elements are situated, and the axes of rotation may be offset by 90° from each other. The swivel joint may be configured as a planar, double-gimbal swivel joint. Thus, the two swivel elements are gimbal-mounted within a single implant component borehole, with an outer swivel element being rotatably supported in the borehole of the osteosynthesis implant component and the inner swivel element being rotatably supported in the borehole of the outer swivel element.

The connecting elements may be shafts that are pivot-mounted in at least one swivel element and in the implant or implant component. In addition, the swivel elements and the implants or implant components may be separated by slots extending to the connecting elements. which may be in the form of generally arcuate or circular segments.

The implant incorporating the swivel joint may be a block-shaped bone plate, and the thickness of the swivel element and connecting elements may be less than the thickness of the bone plate, other implant, or the wall of an osteosynthesis implant component accommodating the swivel joint. The swivel joint is integrated with the bone plate.

In another preferred embodiment, the swivel joint is integrated in a mounting head for connecting a pedicle screw to a longitudinal support within a spinal vertebra fixation system. The swivel joint includes at least one swivel element, with the mounting head serving to connect the longitudinal support to the pedicle screw. The swivel joint and mounting head may be an integral unit. The implant may be configured as an intervertebral unit or as a vertebra substitute. Such an intervertebral unit may have a swivel joint integral with its top and bottom surfaces for adapting to adjacent vertebra.

In a further preferred embodiment, two swivel joints are attached by their inner swivel elements to the ends of a rod in a direction generally perpendicular to their axes of rotation, with one swivel element of each swivel joint being connected to a vertebral end plate. The vertebral end plates contacting the vertebrae are in the form of oval rings which are connected to outer swivel elements and each outer swivel element, in turn, is connected to each respective inner swivel element. Each of the two vertebral end plates is connected to the rod by way of a swivel joint, each rotatable around at least one axis of rotation.

The swivel joint may be configured for holding a bone fastener. A bone screw or pedicle screw may extend through a borehole in the swivel element, with the screw head bearing against the swivel element, so that the swivel joint permits the screw head to rotate within the bone plate or vertebral fixation system about at least one axis. The borehole in the swivel element may be tapered and a bone fastener such as a bone screw or pedicle screw may have a correspondingly conical screw head so as to permit an angularly fixed connection between the implant or implant component and the bone fastener. Furthermore, the borehole in the swivel element may be provided with internal threading to be engaged by external threading on the screw head or shank of the bone screw or pedicle screw, thus permitting an angularly fixed connection between the implant or implant component and the bone fastener. The threading may be tapered.

The bone screw or the pedicle screw may be provided with an expandable head, and by means of a clamping screw, the parts of the expandable screw head are pressed with a positive fit against the wall of the borehole so as to permit an angularly fixed connection between the implant or implant component and the bone fastener.

Figure 1B:
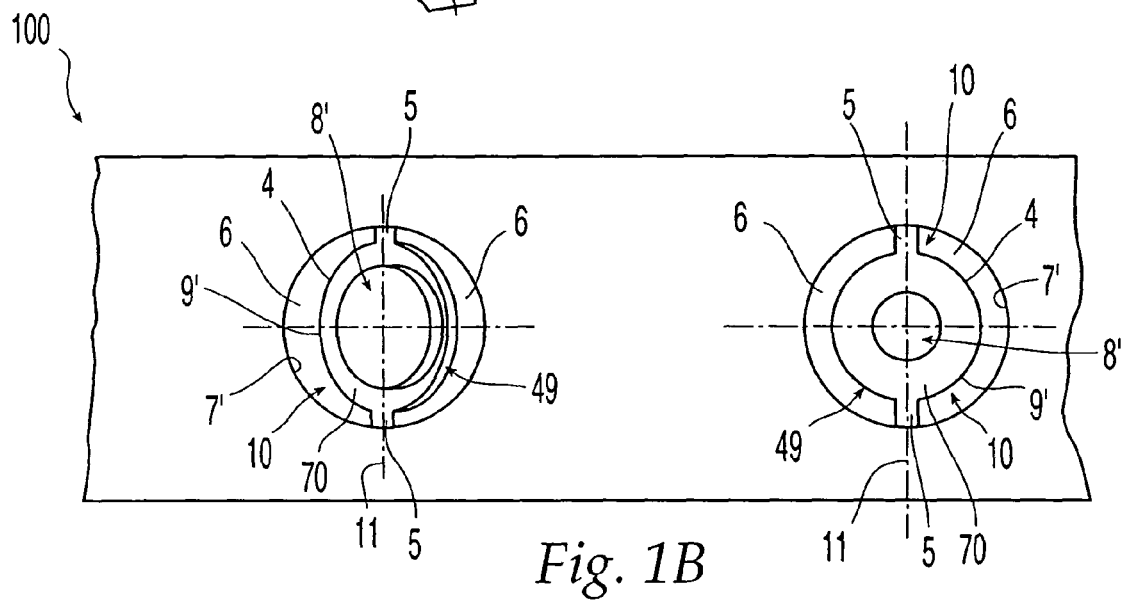
FIG. 1B shows a top view of the implant of FIG. 1A.

Referring to FIGS. 1A and 1B, bone fixation system 100 includes bone plate 3 with couplings 10 in the form of swivel joints 49 mounted therein. In a preferred embodiment, bone plate 3 is provided with at least one screw hole 7 that extends from top surface 13 to bottom surface 14 of bone plate 3 about a center axis 12 and serves to accommodate a fastener 1 such as a bone screw. Screw hole 7 has an inner wall 7'. Swivel joint 49 including a circular inner swivel element 4 and two coaxial inner connecting legs 5. Inner connecting legs 5 connect inner swivel element 4 to bone plate 3. Preferably, inner swivel element 4 has an annular shape, with a central borehole 8' and an outer perimeter 9'. When circular inner swivel element 4 with inner connecting legs 5 is disposed in screw hole 7, two near semicircular slots 6 are defined between wall 7' of bone plate 3 and perimeter 9' of inner swivel element 4, the slots 6 being concentric with screw hole 7. Preferably, slots 6 are milled into bone plate 3, although slots 6 may be formed otherwise. Inner connecting legs 5 and inner swivel element 4 may be unitarily constructed from the same blank and are integral parts of bone plate 3.

Inner swivel element 4 of swivel joint 49 has a thickness $T_a$ defined vertically between upper swivel element surface 70 and lower swiveling element surface 72, and bone plate 3 has a thickness $T_b$ defined vertically between top surface 13 to bottom surface 14. Preferably, legs 5 have a thickness that is substantially the same as thickness $T_a$. In the preferred embodiment, thickness $T_a$ of coupling 10 is less than the thickness $T_b$ of plate 3.

As shown in FIGS. 1A and 1B, coupling 10 with inner connecting legs 5 is in the form of a single gimbal or universal joint. Coaxial connecting legs 5 of swivel joint 49 define an axis of rotation 11 that is disposed transverse to the longitudinal direction of bone plate 3. When a bone screw 1 is inserted into central borehole 8' of inner swivel element 4 and screw head 2 of bone screw 1 bears against upper swivel element surface 70, swivel joint 49 permits rotation of inner swivel element 4 about axis of rotation 11. Thus, bone screw 1 may be oriented at a desired angle and screwed into a bone.

Figure 2:
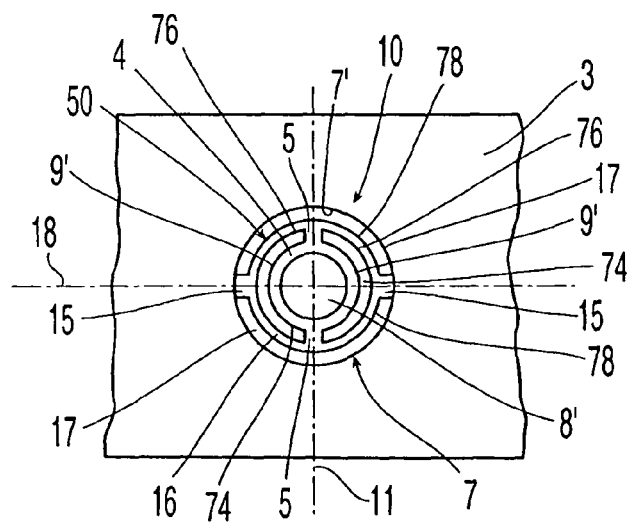
FIG. 2 shows a top view of another implant of the present invention in which a double-gimbaled swivel joint is integrated in a bone plate.

Turning now to FIG. 2, another preferred embodiment of coupling 10 for use with a bone fixation system 100 is shown. Swivel joint 50 is provided with a circular outer swivel element 16 having outer connecting legs 15. A circular inner swivel element 4 is coupled to circular outer swivel element 16 with inner connecting legs 5, while circular outer swivel element 16 is coupled to bone plate 3 with outer connecting legs 15. Two near semicircular slots 74 are defined between perimeter 9' of inner swivel element 4 and first perimeter 76 of outer swivel element 16. Likewise, two near semicircular slots 17 are defined between second perimeter 78 of outer swivel element 16 and wall 7' of bone plate 3. Outer connecting legs 15 are disposed coaxially about an axis 18, permitting outer swivel element 16 to rotate about axis 18.

In the embodiment of FIG. 2, axis 18 is disposed generally parallel to the longitudinal direction of bone plate 3, while axis 11 is disposed generally transverse thereto. Thus, swivel joint 50 permits swivelling about two non-parallel axes 11, 18. Preferably, axes 11, 18 are offset by about 90° with respect to each other, permitting double-gimbaled action. Inner swivel element 4, inner connecting legs 5, outer connecting legs 15 and outer swivel element 16 may be unitarily constructed as integral parts of bone plate 3. Alternatively, inner connecting legs 5 and outer connecting legs 15 may be pins or other suitable coupling elements. If pins are used, the pins forming connecting legs 15 are supported in bone plate 3 and inner swivel element 4, while the pins forming legs 5 are supported in outer swivel element 16 and inner swivel element 4.

Figure 3:
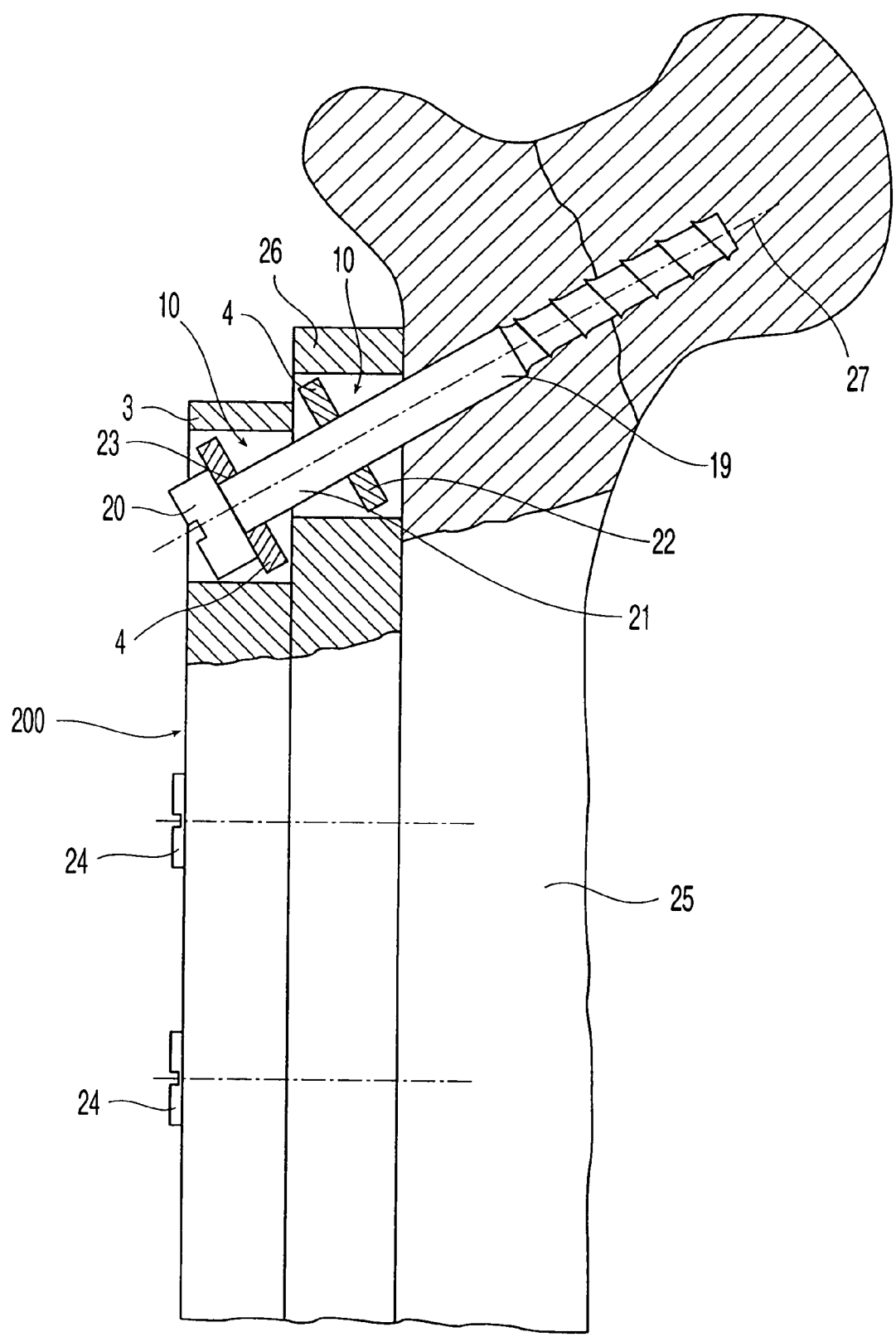
FIG. 3 shows a partial, cross-sectional view of yet another implant of the present invention in which swivel joints are integrated in two femur plates and receive a hip screw.

Referring to FIG. 3, a bone fixation system 200 includes a bone fastener in the form of a hip screw 19 along with upper and lower bone plates 3, 26, each having a coupling 10. Hip screw 19 may enter bone plate 3 at an oblique angle, and thus may be supported in bone plate 3 by means of a coupling 10 such that screw head 20 of hip screw 19 bears against inner swivel element 4 of coupling 10. Preferably, since hip screw 19 does not extend perpendicular to bone plate 3, inner swivel element 4 is tilted in the desired direction prior to implantation of hip screw 19. However, angulation in vivo by a surgeon also may be achieved. A coupling 10 suitable for use in bone fixation system 200, for example, may be in the form of either swivel joint 49 or 50, although embodiments of coupling 10 with more than two swivel elements forming a swivel joint may also be used. Accordingly, depending on the type of joint used, coupling 10 may include inner connecting legs 5 for a single gimbal joint, or coupling 10 may incorporate inner connecting legs 5 and outer connecting legs 15 for a double gimbal joint.

Since inner connecting legs 5 and outer connecting legs 15 preferably provide fixed connections between bone plate 3 and inner swivel element 4, or between bone plate 3, inner swivel element 4 and outer swivel element 16, orientation of a coupling 10 in bone plate 3 may generate a retractive force. It is desirable to minimize or eliminate such retractive forces, as by effectively neutralizing the retractive forces through the use of an additional coupling 10 in a bone plate 26. In particular, upper and lower bone plates 3, 26 are placed one on top of the other, and shank 21 of hip screw 19 is inserted through the integrated coupling 10 of each plate. Additional tightening bone screws 24 may be used for fastening the two bone plates 3, 26 to bone 25.

By moving bone plates 3, 26 relative to each other, it is possible to adjust and fix the orientation of hip screw 19 in a wide range of angles. Tightening bone screws 24 may be used to fix bone plates 3, 26 in place, and additionally serve to fix the orientation of hip screw 19. Shank 21 of hip screw 19 is inserted in central boreholes 22, 23 of inner swivel elements 4 of couplings 10 which are provided in bone plates 26, 3, respectively. Due to the use of two couplings 10, when bone plates 3, 26 are fastened, forces transverse to longitudinal axis 27 of hip screw 19 are avoided, notwithstanding the retractive force of inner connecting legs 5 and outer connecting legs 15.

FIGS. 4A, 4B and 4C show another preferred embodiment of the present invention in the form of a vertebral fixation system 300. Coupling 10 is used to connect pedicle screw 29 to mounting device 34, which has a first end 80 and a second end 82. Preferably, first end 80 of mounting device 34 is configured for threadable engagement with a fastening nut 33, so that the location of mounting device 34, and consequently the position of pedicle screw 29, may be fixed on a longitudinal support 32 that extends through a borehole 86. A coupling 10 is disposed in second end 82 of mounting device 34, and preferably coupling 10 includes an inner swivel element 4, an outer swivel element 16, inner connecting legs 5, and outer connecting legs 15, as previously described herein. Inner swivel element 4, outer swivel element 16, inner connecting legs 5 as well as outer connecting legs 15 are all integrated with mounting head 31.

A central longitudinal axis 35 extends between first end 80 and second end 82 of mounting device 34, preferably about the center of a cavity 84 in mounting device 34. Pedicle screw 29 is inserted through borehole 28, defined by inner swivel element 4, until screw head 30 makes full contact with borehole 28. If pedicle screw 29 does not extend parallel to longitudinal axis 35 of mounting head 31, coupling 10 compensates for the change in angle. The choice of design for coupling 10 dictates the permissible angulation of pedicle screw 29. For example, when a swivel joint 50 having a dual-gimbal swivel joint is employed, it is possible to rotate the pedicle screw 29 relative to mounting head 31 about two axes 36, 37. Alternatively, if a coupling 49 with a single gimbal swivel joint is used, the coupling only facilitates the rotation of pedicle screw 29 about one axis relative to mounting head 31.

Figure 5:
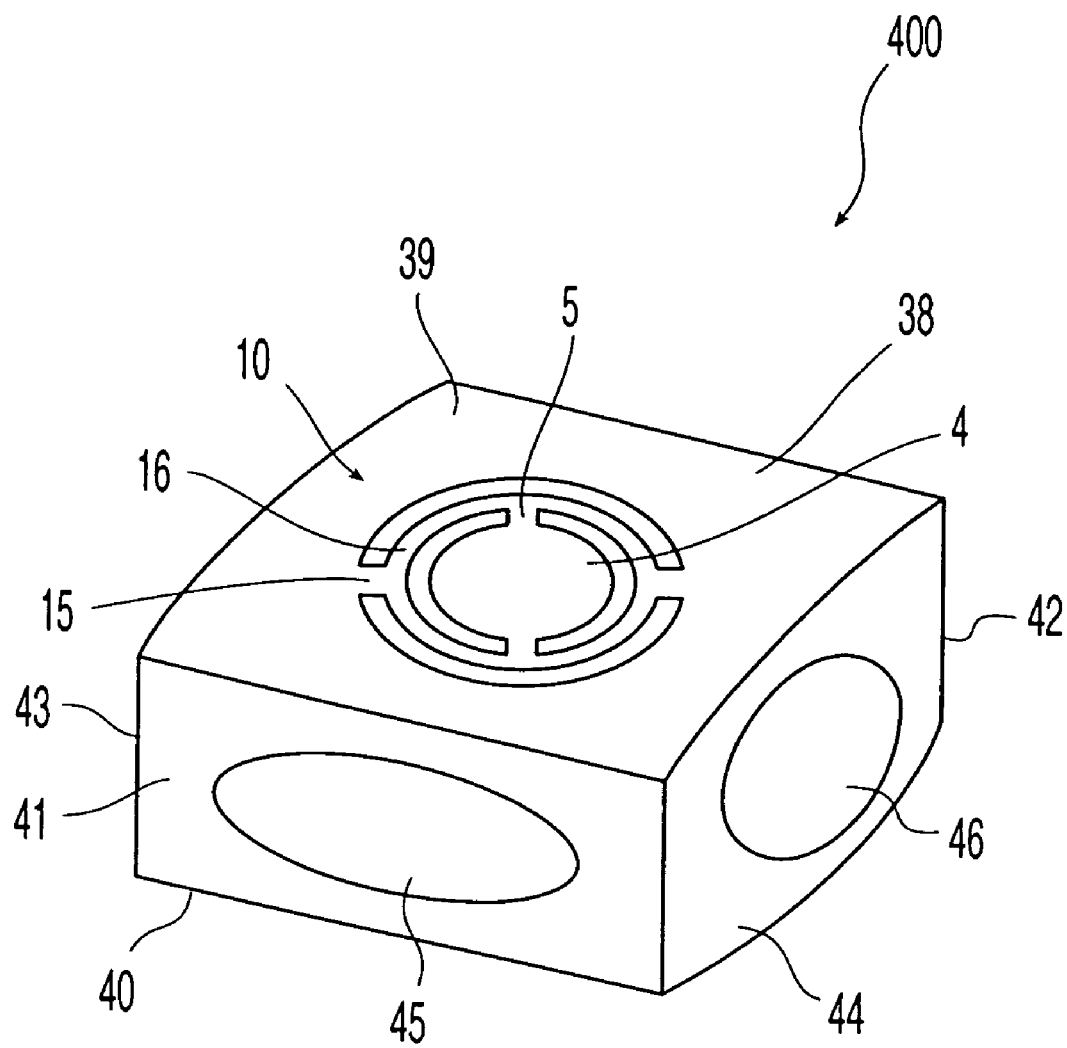
FIG. 5 shows a perspective view of another implant of the present invention in which a swivel joint is integrated in a vertebral unit.

Referring to FIG. 5, another preferred embodiment of the present invention is shown in the form of a spinal block, which may serve as an intervertebral element or as a vertebra substitute. Vertebral fixation system 400 includes a spinal unit 38 with a pair of opposing couplings 10 disposed in the top surface 39 and bottom surface 40. Couplings 10 include inner swivel elements 4, which serve as the support surfaces for vertebral sections adjacent to spinal unit 38 upon implantation. Inner swivel elements 4 may be plate-like or annular, and thus may not include a central hole therein. Spinal unit 38 preferably has the general form of a block, further including a front surface 41, rear surface 42, and two side surfaces 43 and 44. A first through-hole 45 extends from front surface 41 to rear surface 42, and a second through-hole 46 extends between side surfaces 43 and 44.

Preferably, top surface 39 and bottom surface 40 of spinal unit 38 are cambered so that the inner swivel elements 4 of the pair of couplings 10 form the highest point of top surface 39 and the lowest point of bottom surface 40. Advantageously, couplings 10 permit spinal unit 38 to be used even when the lower and upper support surfaces in the spinal column (i.e., adjacent vertebral bodies) are not parallel to one another. Couplings 10 may be integrated into top surface 39 and bottom surface 40 of spinal unit 38, so that spinal unit 38 and couplings 10 are made of unitary construction. With reference to FIG. 2, for example, each coupling 10 may include an inner swivel element 4 having two opposing, coaxial, inner connecting legs 5 that permit rotation with respect to outer swivel elements 16. Outer swivel elements 16 are connected to spinal unit 38 with two opposing, coaxial, outer connecting legs 15 that permit rotation with respect to spinal unit 38. Preferably, outer connecting legs 15 are offset by about 90° with respect to inner connecting legs 5. Thus, each inner swivel element 4 serves as a support surface for the parts of the spinal column that are adjacent to and in contact with spinal unit 38. Furthermore, each inner swivel element 4 preferably permits rotation about two approximately perpendicular axes disposed proximate top surface 39 and proximate bottom surface 40 of spinal unit 38.

Figure 6:
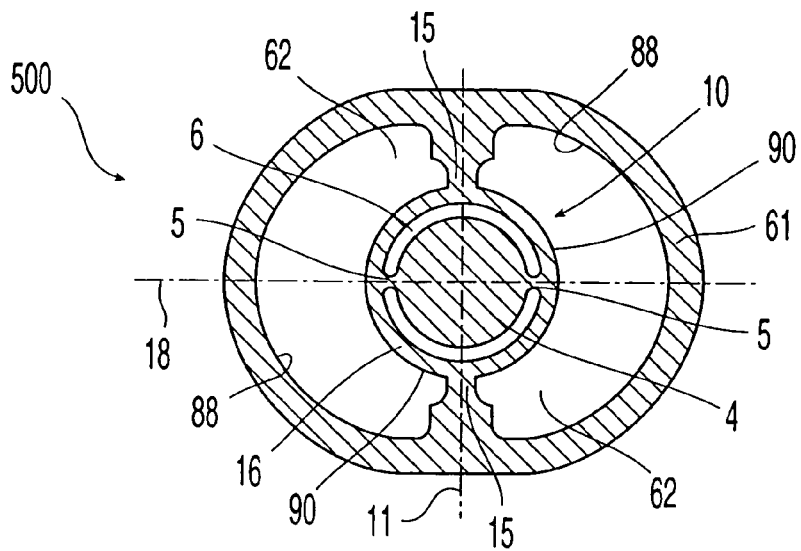
FIG. 6 shows a cross-sectional view of yet another implant of the present invention in which a vertebral unit is integrated with a swivel joint.
Figure 7:
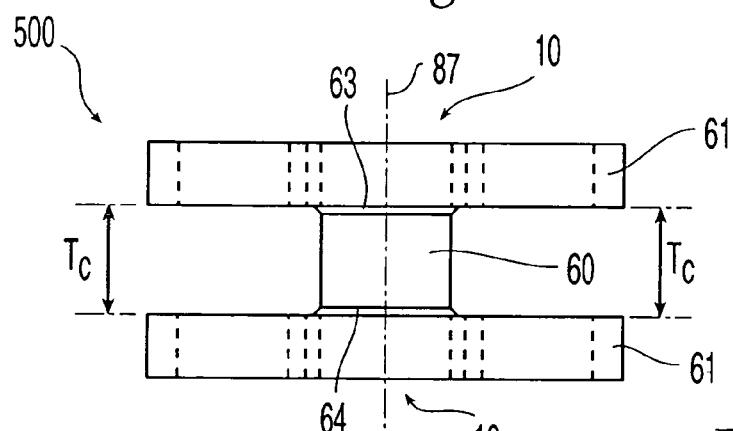
FIG. 7 shows a side view of the implant of FIG. 6.
Figure 8:
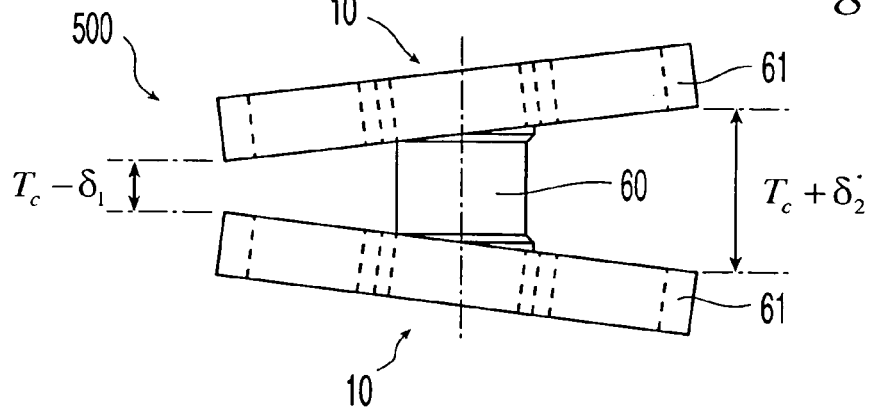
FIG. 8 shows another side view of the implant of FIG. 6 with the vertebral end plates disposed at an angle.

As shown in FIGS. 6-8 another preferred embodiment of the present invention may serve as a spinal implant. Vertebral fixation system 500 includes a pair of vertebral end plates 61 that each have a centrally located coupling 10. Each coupling 10 includes two nested swivel elements 4, 16 connected to each other via connecting legs 5, 15, so that rotation of vertebral end plates 61 is permitted. In the pre-rotation base position, swivel elements 4, 16 are disposed about a common plane formed by axes of rotation 11, 18, which extend parallel to the support surfaces of vertebral end plates 61. Outer annular swivel elements 16 are connected to vertebral end plates 61 with a pair of coaxial connecting legs 15 that generally define axis 11, such that rotation is permitted about axis 11. In addition, outer annular swivel elements 16 are connected to inner swivel elements 4 with generally coaxial connecting legs 5, such that rotation is permitted about axis 18. Preferably, vertebral end plates 61 are in the form of oval rings that define hollow areas 62 between the inner walls 88 of vertebral end plates 61 and the perimeter 90 of outer swivel elements 16.

Moreover, each of the inner swivel elements 4 is attached to one of ends 63, 64 of a central body 60, which may be cylindrical and preferably is a rod. Rod 60 is disposed along central axis 87 which also is generally perpendicular to the plane formed by axes of rotation 11, 18, and thus perpendicular to the pair of opposing, inner swivel elements 4. Each of the two vertebral end plates 61 is connected to rod 60 via a coupling 10 such that rotation is permitted about two axes 11, 18. Referring in particular to FIGS. 7-8, vertebral end plates 61 are show in an initial state in FIG. 7 with a uniform spacing $T_c$ therebetween. The provision of a coupling 10 in each of upper and lower vertebral end plates 61, and the provision of a connection between each coupling 10 of the two plates, permits vertebral fixation system 500 to angulate based on forces applied to plates 61. For example, as shown in FIG. 8, the generally uniform separation distance $T_c$ may be decreased by an amount $\delta_1$ in one region, while the separation distance $T_c$ may be increased by an amount $\delta_2$ in another region of system 500.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, in an alternate embodiment, more than two annular swivel elements may be provided. In addition, the connecting legs that couple the swivel elements to each other and also to an implant may not be disposed generally perpendicular with respect to each other. Still further, the swivel elements may be detachably connectable to a bone plate, so that a surgeon can choose a coupling with a suitable central bore hole size for receiving a bone screw having a surgeon-selected diameter or configuration. In yet another alternate embodiment, fastening elements such as bone screws may be threadably engaged with one or more couplings. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An implant comprising: at least one coupler having at least two connecting elements for engaging a first member to a second member, the connecting elements permitting the first member to rotate with respect to the second member, and wherein the connecting elements are pins pivot-mounted in the first member, the first member being a bone plate having a screw hole extending from a top surface thereof to a bottom surface thereof sized and configured to receive the at least one coupler via the connecting elements.

2. The implant of claim 1, wherein the at least one coupler has an outer perimeter and the connecting elements extend from the outer perimeter.

3. The Implant of claim 1, wherein the at least one coupler has an outer perimeter and the connecting elements are spaced along the outer perimeter along a common axis defining an axis of rotation.

4. The implant of claim 1, wherein the first member has a through hole for receiving the coupler and the at least one coupler includes a borehole for receiving the second member.

5. The implant of claim 4, wherein the connecting elements are concentrically supported in the through hole formed in the first member.

6. The implant of claim 4, wherein the connecting elements are sized and configured for elastic deformation.

7. The implant of claim 1, wherein the at least one coupler comprises a first coupler and a second coupler wherein each coupler has at least two connecting elements and wherein the first coupler has an inner hole sized and configured to receive the connecting elements of the second coupler.

8. The implant of claim 7, wherein the first coupler is connected to the first member via the connecting elements and the second coupler includes a borehole for receiving the second member.

9. The implant of claim 8, wherein the first coupler permits rotation of the first member with respect to the second member about a first axis and the second coupler permits rotation of the first member with respect to the second member about a second axis.

10. The implant of claim 9, wherein the first axis and the second axis are offset with respect to each other.

11. The implant of claim 9, wherein the first axis and the second axis are perpendicular with respect to each other.

12. The implant of claim 1, wherein the connecting elements are tabs which are sized and configured to contact a through hole formed in the first member so that the first member can rotate with respect to the at least one coupler.

13. The implant of claim 1, wherein the second member is a bone screw and the at least one coupler further includes a borehole for receiving the bone screw so that the at least one coupler permits rotation of the bone screw with respect to the bone plate via the connecting elements.

14. The implant of claim 13, wherein the bone plate has a first thickness and the at least one coupler has a second thickness, the first thickness being greater than the second thickness.

15. The implant of claim 13, wherein the borehole formed in the at least one coupler has a tapered surface and the bone screw has a conical screw head sized and configured to contact the tapered surface so that the bone screw can rotate with respect to the at least one coupler.

16. The implant of claim 13, wherein the borehole formed in the at least one coupler includes an inner threading and the bone screw has an externally threaded bone screw head for threadingly engaging the inner threading.

17. The implant of claim 13, wherein the bone screw has an expandable head and means for fixedly securing the head to the borehole.

18. The implant of claim 13, wherein the at least one coupler is a circular element with an outer perimeter having the at least two connecting elements extending from the outer perimeter, wherein the connecting elements are sized and configured to contact the screw hole formed in the bone plate so that the bone screw can rotate with respect to the bone plate about an axis of rotation.

19. The implant of claim 13, wherein the at least one coupler comprises an inner coupler member and an outer coupler member, each member having at least two connecting elements.

20. The implant of claim 19, wherein the outer coupler member has an outer perimeter and an inner perimeter, the outer perimeter being sized and configured to contact the screw hole formed in the bone plate via the connecting elements and wherein the inner perimeter is sized and configured to engage the inner coupler member via the connecting elements, the inner coupler member incorporating the borehole for receiving the bone screw.

21. The implant of claim 20, wherein the connecting elements of the outer coupler member permits rotation of the bone screw with respect to the bone plate about a first axis and the connecting elements of the inner coupler member permits rotation of the bone screw with respect to the bone plate about a second axis, the first axis and the second axis being offset with respect to one another.

22. A bone plate, comprising:
a bone fixation element receiving hole extending through the bone plate along a hole axis from a first surface to a bone contacting surface thereof which, when the plate is mounted on a bone in a desired location faces the bone; and
a coupler pivotally mounted within the bone fixation element receiving hole, the coupler including first and second connecting elements engaging a wall of the bone fixation element receiving hole and including an opening therein for receiving a bone fixation element therein so that the bone fixation element may be pivoted relative to the hole axis.

23. The bone plate of claim 22, wherein an inner wall of the coupler defining the opening is threaded to threadedly engage a threaded head of a bone fixation element inserted therein.

24. The bone plate of claim 22, wherein the first and second connecting elements are positioned on the coupler so that they define two substantially identical slots between an inner wall of the bone fixation element receiving hole and an outer surface of the coupler.

25. The bone plate of claim 24, wherein the slots are substantially semi-circular.

\* \* \* \* \*